United States Patent [19]

Constantz et al.

[11] Patent Number: 5,053,212

[45] Date of Patent: Oct. 1, 1991

[54] INTIMATE MIXTURE OF CALCIUM AND PHOSPHATE SOURCES AS PRECURSOR TO HYDROXYAPATITE

[75] Inventors: Brent R. Constantz, Scott Valley; Bryan Barr, Mountain View; Kevin McVicker, Fremont, all of Calif.

[73] Assignee: Norian Corporation, Mountain View, Calif.

[21] Appl. No.: 558,890

[22] Filed: Jul. 27, 1990

Related U.S. Application Data

[63] Continuation-in-part of Ser. No. 7,393,579, Aug. 14, 1989, abandoned, which is a continuation-in-part of Ser. No. 7,358,716, May 30, 1989, abandoned, which is a continuation-in-part of Ser. No. 7,183,770, Apr. 20, 1988, Pat. No. 4,880,610.

[51] Int. Cl.$^5$ ............................................. C01B 25/32
[52] U.S. Cl. .................................... 423/305; 423/308; 423/309; 423/311; 433/199.1; 623/16; 623/901
[58] Field of Search ................ 423/305, 308, 309, 311

[56] References Cited

U.S. PATENT DOCUMENTS

| 4,429,691 | 2/1984 | Niwa et al. | 423/309 |
| 4,880,610 | 11/1989 | Constantz | 423/305 |

FOREIGN PATENT DOCUMENTS

| 2755751 | 6/1978 | Fed. Rep. of Germany | 623/16 |
| 132713 | 6/1987 | Japan | 423/311 |
| 1331501 | 8/1987 | U.S.S.R. | 623/16 |

*Primary Examiner*—Wayne A. Langel
*Attorney, Agent, or Firm*—Bertram I. Rowland

[57] ABSTRACT

Novel compositions are provided for the production of hydroxyapatite, where a dry mixture is provided which combines a calcium source and an acidic phosphate source, particularly monocalcium phosphate monohydrate or orthophosphoric acid crystals. These two are combined, optionally with other ingredients, with mechanical mixing, resulting in partial reaction or intimate combination to produce a product which requires less water for formation of a desired viscosity, has enhanced mechanical properties and is physilogically acceptable.

18 Claims, No Drawings

INTIMATE MIXTURE OF CALCIUM AND PHOSPHATE SOURCES AS PRECURSOR TO HYDROXYPATITE

This application is a continuation in part of application Ser. No. 393,579, filed Aug. 14, 1989 now abandoned, which is a continuation in part of Ser. No. 358,716, filed May 30, 1989 now abandoned which is a continuation in part of Ser. No. 183,770, filed Apr. 20, 1988, now U.S. Pat. No. 4,880,610.

INTRODUCTION

1. Technical Field

The field concerns the preparation of calcium phosphate products capable of in situ formation.

2. Background

Hydroxyapatite is a naturally occurring calcium phosphate mineral which is the primary constituent of bone. Hydroxyapatite is only one of a number of calcium phosphate minerals, where the ratios of calcium and phosphate differ, the crystal structures differ, as well as the physical characteristics. In addition, many calcium phosphate minerals will include minor amounts of other ions, such as carbonate, magnesium, fluoride, and the like.

Apatite is a general term for a wide range of compounds represented by the general formula $M^{2+}{}_{10}(ZO_4{}^{3-})_6Y^{-2}$, where M is a metal atom, particularly alkali or alkaline earth metal atom, and $ZO_4$ is an acid radical, where Z may be phosphorus, arsenic, vanadium, sulfur or silicon, or may be substituted in whole or in part with carbonate ($CO_3{}^{-2}$). Y is an anion, particularly halide, hydroxy, or carbonate. Hydroxyapatite assumes substantial economic importance in view of its occurrence as a building block in bone, teeth and some invertebrate skeletons. There are many situations where bone has been broken, destroyed, degraded, become too brittle, or been subject to other deteriorating effects. In many of these situations it would be desirable to be able to replace the bone structure or strengthen the bone structure. In providing materials to substitute for natural bone, there are a number of restraints on the nature and composition of the material.

The material should be physiologically acceptable, so as to avoid the initiation of clots, inflammatory response, and the like. The calcium phosphate may be present in a substantially non-resorbable form in vivo (i.e., apatite), particularly where fluoride is present, or in a more resorbable form, where carbonate is present or Ca:P ratio is low (i.e., brushite). In addition, the material must be strong and not friable. Furthermore, there should be strong adhesion between the material and any remaining bone. Also, desirably, the material should be subject to assuming some of the natural role of bone, such as accommodating stem cells, allowing remodeling by osteoclasts followed by new bone ingrowth, and normal metabolic calcium exchange of native bone.

Besides the biological and physiological considerations, there are the additional considerations of how the material is made and the ease with which it may be formed to a desired shape. Specifically, a material which could be injected as a liquid to fill voids and completely fill an area deficient of hard bone is very desirable. Thus, there is substantial interest in having a flowable material.

Where the material is to be placed in situ, a variety of additional considerations come to the fore. For example, the rate at which the reaction occurs for formation of hydroxyapatite, as well as the change in enthalpy of the reaction, are important. Where the reaction is highly exothermic, it may not be tolerated by the patient. The form in which it is introduced must be stable in the environment in which it is introduced, so that not only must the final product be stable, but also the intermediate products as the reaction occurs to form the hydroxyapatite.

It has therefore been found difficult to provide physiologically useful forms of hydroxyapatite and/or other calcium phosphate minerals. For the most part, the hydroxyapatites and other calcium phosphate bone grafting particulates which have been available have lacked one or more of the properties necessary for a useful implant, and, therefore, have failed to obtain general acceptance.

Relevant Literature

Patents of interest include U.S. Pat. Nos. 3,787,900; 3,913,229; 3,679,360; 4,097,935; 4,481,175; 4,503,157; 4,612,053; 4,659,617; and 4,693,986. See also, Arends and Jongebloed, Rec. Trav. Chim. Pays-Bas (1981) 100:3-9. Use of calcium phosphate as a sealer-filler material is described in Chohayeb et al., J. Endodontics (1987) 13:384-387. See also, Ohwaki et al., 13th Ann. Mtg. of the Soc. for Biomaterials, June 2-6, 1987, New York, N.Y., p. 209, Mannes, Mrs. Int'l. Mtg. on Adv. Mats. (1989) 13:15-25. Other references of interest include Ceramic Fabrication Processes (ed. C. Greskovih) Academic Press, 1976, pp. 15-33; Introduction to Processes of Ceramic Processing, (ed. J. S. Reed) John Wiley & Sons, 1988, pp. 255-276; Ceramic Processing Before Firing, P. Somasundaran, John Wiley & Sons, 1978, pp. 105-123; Hogg, Am. Ceramic Soc. Bull. (1981) 60 [2], 206-211; Inorganic Phosphate Materials, 8.2.5. Mechanochemistry (ed. M. Chikazawa), Kodansha, 1989, pp. 212-214, Milewski, Adv. Ceram. Materials (1986) 1 [1]36-41; and Stan, Am. Ceram. Soc. Bull. (1986) 65 [9], 1293-96.

SUMMARY OF THE INVENTION

A calcium source and an acid source of phosphate, preferably having at least two protons per phosphate group, are mechanically intimately mixed and milled, causing a mechano-chemical reaction, resulting in a product which may be combined with other materials to form a calcium phosphate product of high strength and improved mechanical properties. The mechanically induced reaction reduces the requirement for water during the formation of a flowable calcium phosphate cement or calcium phosphate/biopolymer composite.

DESCRIPTION OF SPECIFIC EMBODIMENTS

Methods and compositions are provided for producing bone-like materials comprising structures analogous to the naturally occurring physiologically acceptable calcium phosphate minerals, particularly hydroxyapatite, including carbonated and fluoridated derivatives. The hydroxyapatite composition is formed in substantially two stages: a first stage which involves the mechanical intimate mixing and milling of a Ca-source, e.g., tetracalcium phosphate, and a phosphoric acid source substantially free of uncombined water, desirably having at least two protons per phosphate and not more than about one water of hydration per molecule, and, in addition, other optional additives; and a second stage which involves mixing with water and optionally other additives to provide the final product, which sets up to a calcium phosphate mineral, e.g., an hydroxyapatite, having desirable mechanical properties.

The first stage involves the mechanical mixing of the primary calcium sources. The acidic neutralizing phosphate source will be free of uncombined water and may be ortho-phosphoric acid crystals or monocalcium phosphate monohydrate $(Ca(H_2PO_4)_2) \cdot H_2O$ or other calcium phosphate acid source by itself or in combination e.g., monetite. Ca-sources present will include counterions, such as a source of carbonate, e.g., calcium carbonate, or a source of phosphate, e.g., tetracalcium phosphate, a base, such as calcium oxide or calcium hydroxide, a source of fluoride, such as calcium fluoride, or the like. The ratio of calcium to phosphate will provide for stoichiometries ranging from 1.25:1 to 2:1, allowing preferential formation of a number of stable compounds, including monetite, brushite, octacalcium phosphate, calcium-deficient hydroxyapatite, stoichiometric hydroxyapatite (1.67:1), or composites of the aforementioned minerals, in addition to various metastable amorphous calcium phosphates. By controlling the calcium-to-phosphate ratio, and hence final cement composition, it will be possible to tailor the resorption rate of the cement when administered into the body. The resorption rates will vary from as little as 6 weeks to as much as 18 months.

The reaction of calcium oxide with the acidic phosphate source results in an exothermic reaction. Where the mixture is to be used to set in situ for a bone replacement, high temperatures are undesirable. Desirably, the temperature produced should be below a pain inducing temperature, generally less than 60° C. Generally, the amount of calcium oxide or calcium hydroxide will range from about 0 to 50 weight percent, more usually from about 5 to 30 weight percent, and preferably from about 5 to 15 weight percent of dry weight.

Calcium carbonate provides for some neutralizing capability and substantial buffering capability (e.g., $HCO_3^-$), but results in the production of carbon dioxide. The gas must be expressed and can result in building up of high pressures in a closed milling system. Therefore, when using calcium carbonate or other carbonate, it is essential that means be provided for releasing the pressure or using a system capable of maintaining elevated pressures. Usually, the calcium carbonate will be present in from about 0 to 70 weight percent, more usually from about 0 to 40 weight percent, and preferably from about 2 to 18 weight percent of dry weight.

The tetracalcium phosphate may typically be the major proportion of the mixture, generally ranging from about 55 to 75 weight percent, more usually from about 60 to 70 weight percent of dry weight.

The acid source will generally be about 15 to 35 weight percent, more usually 15 to 25 weight percent.

The source of fluoride will generally be present, if at all, in relatively small amounts, generally ranging from about 0 to 4 weight percent, more usually from about 2 to 4 weight percent, preferably from about 3 to 4 weight percent of dry weight.

The dry ingredients are combined, particularly as powders or small particles, the particular size of the particles not being crucial to this invention, but certain ranges being preferred. Generally, the particles will be smaller than about 500 $\mu$, more usually smaller than about 250 $\mu$ and may range from about 50 Angstroms to 200 $\mu$ on the average. Since small amounts of fine powder will skew the average size, it should be understood that in referring to the average size, the intent is those particles contributing to at least about 80 weight percent of the component, usually at least about 90 weight percent.

Raw material particle size prior to milling or mechano-chemical mixing may be varied in order to choose the particular chemical reaction paths within the milling jar. By decreasing powder size, effective surface area is increased, allowing the initial composition of the reaction products to be altered, consequently affecting the final powder product composition, and hence mechanical, physical, and mixing properties.

Small amounts of organic polymers, particularly proteins, substantially anhydrous, may be included in the mixture prior to completion of the mechanical mixing. A list of proteins is provided subsequently. The amount of additive will generally be from about 1 to 40 weight percent, more usually, 1 to 25 weight percent of the inorganic materials. Desirably, the polymer is added to the inorganic materials before milling, mixed while substantially retaining the bulk of the additive and then introduced into the milling device. Since the bulk will usually be substantially diminished during milling, media should be removed accordingly.

The particular manner in which the various ingredients is combined is not critical to this invention, so long as intimate mixing occurs, partial reaction may proceed between the ingredients without complete reaction. Techniques which may be used include ball milling, Brabender mixing, rolling between one or two rollers in a flexible container, or the like. Various equipment may be used, including ball mills, planetary mills, centrifugal mills, mechanofusion systems, air pulverizers, jet mills, vibratory mills, colloid mills, attrition mills, disc mills, and the like.

The course of the mixing can be monitored by taking aliquots and testing to see whether the aliquots provide for the desired physical properties when mixed with an aqueous medium, by stopping the mixing when undue caking occurs, or by compositional determination via XRD or FTIR. Depending upon the nature of the mixing, the efficiency of the mixing, the size of the particles of the various ingredients, the particular ingredients, and the like, mixing may take as little as 0.5 h and usually not more than about 24 h. In using a ball mill, certain parameters may be optimized. For example, the following equations may be used for rate of surface area production in $m^2/gh$:

$$\text{rate} = \frac{0.045}{} + 0.055 D^{0.65}$$

$$\text{rate} = cpD^{\frac{1}{2}} bd^{-2}$$

$$\text{rate} = cpD^{\frac{1}{2}} bd^{-1}$$

where d is the media (ball) diameter, D is the mill diameter, p is the ball density, b is the particle diameter and c is a constant. It is generally argued that the milling rate varies directly with the diameter of the mill and inversely with the media diameter. Loading of the mill should be about 50% of the mill volume. The media should be as small as possible, but usually at least about 25 times the feed size. The feed should be at least about equal to the void volume between the media, preferably in slight excess. Mill rotation should be about 60-70% of critical speed $54.2/r^{\frac{1}{2}}$, where r is the radius of the mill in feet.

During the milling, walls may be scraped periodically to help promote milling/mixing. The media should be stable and inert under the conditions of the milling, various media being available, e.g., alumina, zirconia, tungsten carbide, boron carbide, etc.

The mixing will be continued until at least about 50% of the acid source has reacted to produce a partially neutralized mixture of calcium phosphate phase compounds, including amorphous calcium phosphates that may differ qualitatively from the initial ingredients.

It is found that a number of advantages ensue by having the intimate mixing with partial reaction occurring. First, the mixture when added to water usually does not go through intermediates which remove water as waters of hydration. Thus, less water needs to be added in order to provide for a workable mixture. The lower amount of water which must be added results in improved mechanical properties of the final product. In addition, the reaction between the base and acid is apparently slowed, while the setting time is reduced. In this way, one achieves a more stable product more quickly. This can be very important where the environment into which the composition is introduced may have a substantial amount of liquid, such as blood, which may be flowing and can modify the properties of the composition, as well as erode the composition away before it sets.

Once the mixture is formed it may be stored for long periods of time without change in composition or characteristics. Desirably, it is stored in an anhydrous environment and a watertight container. If necessary, the product may be sterilized in accordance with conventional ways, using ethylene oxide, elevated temperature, gamma radiation, etc.

The dry composition will be combined with a physiologically acceptable lubricant, conveniently an aqueous lubricant, e.g., sterile water. The water which is used will be substantially pure, such as double distilled, deionized or equivalent thereof. Other hydroxylic materials which are water miscible, pharmacologically acceptable and do not interfere with the calcium mineral formation, may also find use. For example, polyols, such as ethylene glycol, propylene glycol or glycerol may find use in minor amounts, less than about 10 volume percent.

When mixing with the lubricant, a wide variety of other materials may be employed. Various extenders may be employed, particularly grit or gravel of a particle size in the range of about 10 to 250 $\mu$. Desirably, the particles will be dense, sintered and be physiologically acceptable, particularly calcium phosphate particles. Of particular interest is dry calcium phosphate particles of from about 25 to 100 $\mu$ in size. The amount of the particles or aggregate, when used, will generally be at least about 50 weight percent and not more than about 90 weight percent, usually not more than about 80 weight percent, and preferably from about 65 to 75 weight percent of the final mixture. The aggregate is selected so as to form a strong bond with the calcium phosphate matrix, enhance the compressive strength of the composition, and be physiologically acceptable.

In many situations, a wide variety of additives may be included in the medium to provide for specific properties. One group of additives is protein. Bone associated proteins may be added to modify the physical properties of the composition, enhance resorption, angiogenesis, cell entry and proliferation, mineralization, bone formation, growth of osteoclasts and/or osteoblasts, or the like. Proteins of particular interest are the different types of collagen, particularly Type I. Other proteins include osteonectin, bone sialoproteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenetic protein, cartilage induction factor, platelet derived growth factor and skeletal growth factor. Other proteins associated with other parts of human or other mammalian anatomy, include proteins associated with cartilage, such as chondrocalcining protein; proteins associated with dentin, such as phosphophoryn, glycoproteins and Gla proteins; or proteins associated with enamel, such as amelognin and enamelin.

Other proteins of interest include fibrin, fibrinogen, keratin, tubulin, elastin, and the like. Blood proteins may be employed, individually or together, in plasma or serum, e.g., serum albumin.

Alternatively, as previously indicated, the protein may be combined with the acid source and the Ca-source prior to milling or curing in a dried form so as to create intimate mixing and combination with the inorganic constituent of the cement. When added after milling the proteins will generally vary from about 0.1 to 5, more usually 0.2 to 2 parts of protein based on calcium phosphate mineral, as an aqueous dispersion or solution. Usually, the protein will be present in from about 1 to 80 weight percent of the aqueous dispersion. The amount of water added as the protein dispersion will be added in combination with the lubricant, where the total amount of water will come within the total amount of lubricant.

When the protein is added prior to milling, the mineral powders/crystals are weighed out and ground, e.g., with a mortar and pestle. The protein, e.g., collagen, is gradually and gently mixed into the mineral powder such that the mineral powders coat the protein material and the bulk volume of the protein is retained. The composite material is then gently ground while still maintaining the majority of the bulk volume of the composite. This composite material is placed into a mill jar with appropriate media loading for the bulk volume. After 2–4 hours, half the media needs to be removed adjusting to the decreasing bulk volume as ball milling progresses. The material is milled for about 8–24 hours.

Various other additives may be included to modify the physical structure of the final product. Various water soluble physiologically acceptable materials may be included in minor amounts, e.g., calcium carbonate, calcium sulfate, and NaCl (halite). Sugars, such as sucrose, glucose, or fructose may be included to enhance porosity. The weight of the sugar will usually not exceed 5 weight percent of the total solids.

The amount of lubricant which is used, will generally be from about 15 to 70, more usually from about 25 to 45 weight percent of the entire composition. Preferably, lower amounts of water are used to provide for higher compressive strength and accompanying mechanical properties. The amount of water which is used will be calculated in relation to the amount of water which is formed by reaction of the dry ingredients, so that in referring to the total amount of lubricant, this will include the water produced by the reaction, as well as the water added to the mixture.

The dry ingredients and the wet lubricating medium are combined and thoroughly mixed, so as to provide for a substantially uniform dispersion of the dry ingredients in the lubricant. Once the mixture is uniformly dispersed, it may then be mechanically dispersed, by kneading, rolling, sonicating, or the like. During the mixing, any gas which is formed should be released and the product may be shaped into any appropriate form. The mixing with the lubricant is over a relatively short time, usually not less than about 0.5 minutes and not more than about five minutes, usually not more than about 3 minutes. Where the product is to be introduced in situ, it may be injected into the appropriate site, using a syringe or catheter or packed in by other means, as appropriate.

The product is now allowed to set, during which time crystals grow and the product becomes a single integral mass. While the product may harden almost immediately, usually the maturing process should take at least about 2 min, usually about 8 min and not more than about 30 min, usually not more than about 25 min. Alternatively, where the material has been introduced at a site where it is to be retained, the material will naturally harden over time.

The physical properties of the final product may be varied, depending upon the particular ions which are used in the formation of the product. Microstructure may also be varied, since the shapes and size of the crystals can be varied with resulting variation in the mechanical and biological properties of the product. Also, bulk permeability may be changed in relation to the particular application, where a permeable or impermeable product is desired. The surface area may also be modified where a high surface area may be desirable, for example, up to about $10m^2/gm$, to enhance protein binding, particularly charged proteins.

The subject products may be used for a variety of purposes, such as any form of connective tissue replacement, including bone cement, an injected prosthetic implant, a prosthetic orthopedic or dental implant, as a root canal filler, a prophylactic injection to augment weak osteoporotic bone, a bone plug, or a vehicle for drug delivery. The composition may be used as a paste, being applied to a surface for adherence or holding some structure in place.

The subject compositions may be used with other materials to provide for specific types of properties. Various additives may be employed which add additional tensile strength or fracture toughness, provide for enhanced flexibility, or the like. For example, fibrous materials may be employed, both organic and inorganic, such as silicon carbide whiskers, hydroxyapatite fibers, mineralized collagen fibers, metallic fibers, or the like. See, for example, U.S. Pat. No. 4,503,157.

Where a porous structure is desired, various additives may be included which may be leached out, so as to provide for porosity in the mixture, in addition to any porosity achieved with the release of gas formed during the reaction to produce the product. Aggregates of soluble materials above 25 volume percent will generally develop interconnected tunnels for bony ingrowth. Usually, the aggregate will be less than about 50 volume percent. Porosity may also be achieved by the particular anions and cations employed, where alkali metal salts are produced which are readily dissolved in the medium in which it is allowed to harden. Thus by adding calcium chloride and sodium or potassium hydroxide, the resulting salt will be water soluble and its dissolution will result in pathways through the structure. Similarly, one may include various water soluble fibers, particles, or the like, in the composite structure, which may also be leached out to provide for porosity. Thus, the method of preparation allows for varying the characteristics of the final product.

The viscosity of the product may be varied depending on the application. By varying the product composition, percentage of solids, and presence of other additives, the viscosity may be selected to allow for ease of administration to the site to be treated. By increasing the amount of lubricant in the paste, which occupies space in the final product, the loss of the lubricant will result in a void or pore. Use of flowable materials such as smectite clay (e.g., bentonite) may allow one to lower the amount of liquid, but leaves the clay in final product. Gas evolution from the face may also create voids in the crystallizing product. Thus, porosity may be controlled by adjusting the amount of lubricant and gas evolution. For example, with calcium carbonate as a calcium source, porosity may be reduced by using dilute hydrochloric acid as the lubricant, where the reaction of the acid with the carbonate will result in gas evolution before the paste thickens. Thus, the carbon dioxide will be lost before the formation of the product, resulting in low porosity, while there will be little if any carbonate to become incorporated into the final product. In general, as porosity increases, the compressive strength of the crystallized material decreases.

When desired, very high compressive strengths may be achieved, usually in excess of 5000 psi, preferably in excess of 10,000 psi and optimally in excess of 15,000 psi. Final compressive strengths may be substantially achieved within fewer than about 8 hours, preferably fewer than about 4 hours. Time to one-half of the final compressive strength may be fewer than 5 hours, preferably fewer than 3 hours.

In addition, by having various proteins in the lubricant, the physical characteristics of the product will vary. When adding collagen to the paste the crystallography of the final product is substantially unaffected, while the mechanical properties vary distinctively. The material appears viscoelastic, rather than having linear elasticity and brittleness, and appears to be more abrasion resistant. These properties indicate increased fracture toughness and resistance to fatigue.

Kits may be provided to prepare the subject compositions. Thus, the dry ingredients may be mixed and provided in a sealed container as previously indicated. The lubricant may be provided as a separate container, conveniently a syringe, where the syringe may be used to add the lubricant to the dry ingredients, the dry ingredients mixed, and then taken up into the syringe for administration at the desired site. Where the product is to be used for other than an in situ application, the wet and dry ingredients may be mixed, the product molded and allowed to harden to the final product.

The following examples are offered by way of illustration and not by way of limitation.

EXPERIMENTAL

A number of dry formulations were prepared having the compositions as set forth in the following Table.

TABLE 1

| Ingredients | 1 | 2 | 3 | 4 | 5 |
| --- | --- | --- | --- | --- | --- |
| Tetracalcium phosphate | 45.0 | 56.95 | 6.0 | 43.95 | 13.73 |
| Calcium Oxides | 0.17 | | 0.13 | 0.33 | 0.56 |
| Calcium Carbonate | 5.85 | | 0.95 | 11.4 | 4.0 |
| $Ca(H_2PO_4)_2.H_2O$ | 15.5 | 11.20 | 2.5 | | |
| Orthophosphoric acid | | | | 11.76 | 4.41 |

TABLE 1-continued

| Ingredients | 1 | 2 | 3 | 4 | 5 |
|---|---|---|---|---|---|
| $Na_2SiF_6$ | 0.29 | | 0.04 | 0.25 | 0.09 |

Each of the above formulations were ball milled in an alumina/silica mill jar with 0.5"×0.5" alumina cylinders, where the container was from 25 to 50 volume percent full. The milling usually was continued for about 16 hours. In many cases, some caking was observed, particularly at the top of the container. The gasket at the top of the container to enclose the cover was cut, so as to allow for the release of gas. The mixing was at about 50 rpm.

After completion of the milling, the composition was combined with water, generally using about 0.35 parts of water to 1 part of solids. For preparing samples, 5 grams of the solid mixture was combined with 1.75 grams of deionized water and the mixture kneaded for about 5 min. The composition was introduced into a mold, allowed to set, and the sample removed for tensile strength testing. In some instances, the samples could not be easily removed from the mold, which could have affected the observed tensile properties. The following Table indicates the results, where the results are reported as the average of from 3 to 4 determinations on different samples from the same composition.

TABLE 2

| Ex. | Weight (g) | Load (lbs) | Compressive Strength (psi) |
|---|---|---|---|
| 1. | 0.72 | 367.9 | 8389 |
| 2. | 0.76 | 380.7 | 8677 |
| 3. | 0.74 | 388.7 | 8867 |

Considerable variation was noticed in the results, where in example 3, the variation was from 5002 to 11158, while in example 1, the variation was from 5620 to 11794. Thus, while samples can be obtained having compressive strengths in substantial excess of 10,000 psi, the reasons why other samples from the same composition do not provide the same properties is presently not understood. However, in any sample, products having properties in substantial excess of 10,000 psi compressive strength are achievable.

Cement powders were prepared using an initial powder mixture of the following composition: 0.1937 g CaO, 50.52 g $Ca_4(PO_4)_2O$, 6.56 g $CaCO_3$, 17.39 g $Ca(H_2PO_4)_2 \cdot H_2O$ and 0.3242 g $Na_2SiF_6$. Four powders were produced, changing only $Ca_4(PO_4)_2O$ (CT) particle size prior to milling for 15 hours in a milling jar with $Al_2O_3$ media. The resulting powders were analyzed by XRD, and when hydrated, tested for pH at mixing, set time when submerged in serum at 37° C., and strength at 24 hours. In addition, a $CaCO_3$ aggregate (100 μ) was added after milling to one formula in two volume percentages, and effects on pH and strength noted.

Physical results are summarized in the table below.

TABLE 3

Properties of Cement According to CT Particle Size or Aggregate Addition

| CT Size | Aggregate | Mix pH | Set Time | Compressive Strength |
|---|---|---|---|---|
| −15μ | — | 6.4 | 7 min | 10,000 psi |
| −45μ | — | 6.8 | 6 min | 8,300 psi |
| 45-90μ | — | — | 8 min | — |
| 90-180μ | — | 6.8 | 11 min | 13,000 psi |
| 90-180μ | 17 v/o | — | — | 8,600 psi |
| 90-180μ | 25 v/o | 7.4 | 10 min | 6,500 psi |

By XRD it was determined that the finer CT particles reacted during milling preferentially over $CaCO_3$ bases, whereas larger initial CT allowed $CaCO_3$ to be depleted. These variations had a noticeable effect on both strength and set time of the materials after mixing with $H_2O$.

Aggregate addition caused the pH at mixing to be slightly higher than that of cement matrices alone. Set was slightly enhanced, while compressive strength dropped significantly. As $CaCO_3$ will resorb in vivo quickly, leaving a porous hard matrix, this drop in strength is not of great concern.

In the next study, four samples were prepared from monetite or $Ca(H_2PO_4)_2 \cdot H_2O$ ("MCPM") (fully humidified) and tetracalcium phosphate ("CT") with an overall Ca/P ratio of 1.67:1.

The monetite and MCPM were from J. T. Baker. The preparations were as follows: (A) monetite and CT (45-90 μ) mixed in a bottle by vigorous shaking; (B) monetite and CT (45-90 μ) milled in a 0.33 L milling jar with $Al_2O_3$ rods and ball milled for 6 hrs. The walls were scraped at one hr. intervals; (C) monetite milled as described in (B) followed by mixing with −45 μ CT by vigorous shaking; and (D) MCPM and CT (45-90 μ) milled together as described in (B).

The setting time was determined using the Gillmore needle method using a 0.25 lb weight. The sample was prepared using 1g powder and 0.38 ml water which were mixed in a mortar and pestle for 2 min, the mixture transferred to a 1×12×25 mm mold and the open surface smoothed flat. The assembly was immediately placed in a humidifier at 37° C. and 98% humidity and the sample tested every 4 min, keeping the testing time as brief as possible, until the needle impression was no longer visible.

For determining compressive strength, the milled samples were mixed with deionized water as described above and then loaded into a 6 mm dia., 12 mm high stainless steel die (mold release applied). After packing the die, the sample was compressed for a few seconds under a 6 kg load, refilled and compressed again under a 6 kg load. The dies were then overfilled, placed between damp filter paper, sealed in small plastic bags and the bags placed in the humidifier described above. Packing required from 6 to 9 min. Each material was tested after 1, 3, and 24 hour set times, to indicate the effect of milling history on development of compressive strength with time. After removal from the humidifier, samples were lightly sanded (150 grit) to remove excess material, the sample removed from the die, weighed, measured and then tested on an Instron Model 4202 machine at 0.1 in/min travel. Samples were placed at the center of machine platens and the maximum load determined.

The following table indicates the results:

| Sample | Set Time Minutes | Compression PSI | Mixing Texture |
|---|---|---|---|
| A | 22 | 0 | Wet, gritty |

| Sample | Set Time Minutes | Compression PSI | Mixing Texture |
|---|---|---|---|
| B | 19 | 3300 | Smooth, workable |
| C | 38 | 1800 | Develops wet Texture |
| D | 9 | 5800 | Wet, workable |

D appeared to reach its maximum compression in about 4 hours, while B and C appeared to approach their maximum strength at greater than about 20 hours.

A collagen-containing formulation was prepared as follows. A powder mixture of CaO (0.27 g), $Ca_4(PO_4)_2O$ (50.53 g), $CaCO_3$ (6.56 g), $Ca(H_2PO_4)_2 \cdot H_2O$ (17.39 g), and $Na_2SiF_6$ (0.32 g) was mixed in a pestle, 13.24 g collagen added, and the mixture mixed in a mortar and pestle while retaining bulk volume, then introduced into a ball mill (00 jar size) with spherical media and milled for 16 hrs. 250 ml of media were removed after 4 hrs.

It is evident from the above results, that the subject compositions provide for numerous advantages. First, the dry ingredients can be provided as a dry powder which is premixed, so that it can be delivered to the user in a form which is readily applicable. By taking the dry powder and mixing it with an appropriate lubricant, which can also be provided, the mixture can be readily formed into a paste and be used as desired. The product provides for excellent tensile properties and sets up rapidly to a hard product in a wide variety of environments. The composition is physiologically compatible and, therefore, can be used as a flowable product and introduced at various sites in the body.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. In a method of preparing a product for preparation of a calcium phosphate mineral product, the improvement which comprises:
   mechanically mixing under reaction causing conditions as reactants at least one calcium source and an acidic phosphate source free of uncombined water for sufficient time for partial reaction of said calcium source and acidic phosphate source,
   whereby a dry product is produced for combination with a lubricant to form a solid product with substantially complete reaction of said reactants.

2. A method according to claim 1, wherein said calcium source is tetracalcium phosphate and at least one other basic calcium compound.

3. A method according to claim 2, wherein said acidic phosphate source is ortho-phosphoric acid crystals or mono-calcium phosphate or its monohydrate.

4. A method according to claim 1, wherein an organic polymer in substantially anhydrous form is added not later than completion of said mixing.

5. A method according to claim 1, wherein said reactants provide a calcium to phosphate mole ratio of about 1.25–2.0 to 1.

6. A method according to claim 1, wherein said reactants are powders of a size less than about 500 microns.

7. A method according to claim 1, wherein said lubricant is aqueous and comprises a protein.

8. A method according to claim 1, wherein a protein in substantially anhydrous form is added not later than completion of said mixing.

9. A method according to claim 4, wherein said organic polymer is a protein.

10. In a method of preparing a product for preparation of a hydroxyapatite product, the improvement which comprises:
    mechanically mixing with milling under reaction causing conditions reactants tetracalcium phosphate and an acidic phosphate source free of uncombined water for sufficient time for at least five weight percent of said tetracalcium phosphate and acidic phosphate source to react,
    whereby a dry product is produced for combination with a lubricant to form a solid hydroxyapatite product with substantially complete reaction of said reactants.

11. A method according to claim 10, wherein a protein is combined not later than completion of said mechanically mixing.

12. A method according to claim 11, wherein said protein is collagen.

13. A method according to claim 10, wherein said reactants comprise a minor amount of at least one of calcium oxide and calcium carbonate.

14. A method according to claim 10, wherein said acidic phosphate source is ortho-phosphoric acid crystals or mono-calcium phosphate or its monohydrate.

15. A method according to claim 10, wherein said reactants are powders of size less than about 500 microns.

16. A method according to claim 10, wherein said lubricant is aqueous and comprises a protein.

17. A method according to claim 16, wherein said protein is collagen.

18. A method according to claim 10, wherein said mechanical mixing is ball milling.

* * * * *